United States Patent

Veber

[11] 4,190,648
[45] Feb. 26, 1980

[54] PEPTIDES HAVING SOMATOSTATIN ACTIVITY

[75] Inventor: Daniel F. Veber, Ambler, Pa.

[73] Assignee: Merck & Co., Inc., Rahway, N.J.

[21] Appl. No.: 20,148

[22] Filed: Mar. 13, 1979

[51] Int. Cl.² ............... A61K 37/100; C07C 103/52
[52] U.S. Cl. ........................... 424/177; 260/112.5 S
[58] Field of Search ............... 260/112.5 S, 112.5 R; 424/177

[56] References Cited

U.S. PATENT DOCUMENTS 4,146,612  3/1979  Veber ..................... 260/112.5 S

OTHER PUBLICATIONS

Immer, H., Proceeding of Fourteenth European Peptide Symposium, 471–476 (1976).
Shemyakin, M., et al., Angew Chem., Int. Ed. Engl., 8, 492–499 (1969).

*Primary Examiner*—Delbert R. Phillips
*Assistant Examiner*—Blondel Hazel
*Attorney, Agent, or Firm*—David L. Rose; Harry E. Westlake

[57] ABSTRACT

Peptides having the structural formula:

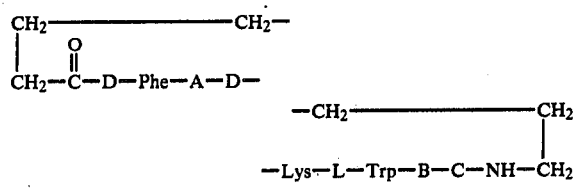

and

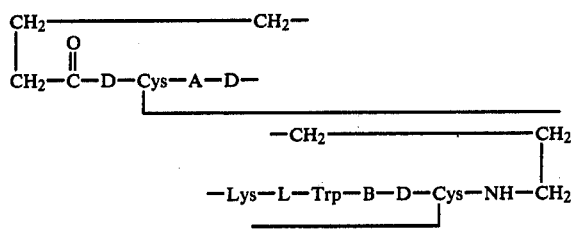

wherein

A is D-Thr, D-Val;

B is D-Phe, D-Tyr;

C is D-Phe, D-Tyr, O-Me-D-Tyr;

wherein the ring formed by the peptide backbone contains 26 atoms and pharmaceutically acceptable nontoxic acid addition salts thereof are prepared by the solid phase method. These peptides have the property of inhibiting release of insulin, inhibiting growth hormone release and inhibiting glucagon release in humans and animals without materially affecting gastric secretion. They have a longer duration of action than somatostatin.

3 Claims, No Drawings

PEPTIDES HAVING SOMATOSTATIN ACTIVITY

BACKGROUND OF THE INVENTION

Somatostatin is a tetradecapeptide having the structure: Ala—Gly—Cys—Lys—Asn—Phe—Phe—Trp—Lys—Thr—Phe—Thr—Ser—Cys—OH and has the properties of inhibiting the release of growth hormone, inhibiting the release of insulin and glucagon and reducing gastric secretion. This lack of specificity of the biological activity of somatostatin has led to an intensive search for analogs which exhibit a more specific biological activity. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

Further efforts to provide peptides having a more specific biological activity and longer duration of activity than naturally occurring somatostatin and which are easier to prepare because of the smaller ring size have resulted in peptides having the structural formula:

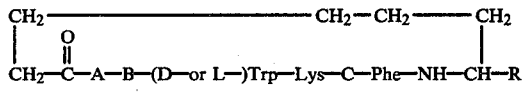

wherein
A is Phe, Tyr, O—Me—Tyr,
B is Phe, Tyr,
C is Thr, Val,
R is H or COOH,
wherein the ring formed by the peptide backbone contains 26 atoms and wherein the preferred peptide is illustrated by the following structural formula:

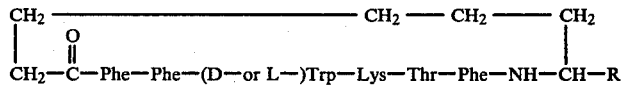

wherein
R is H or COOH, and the pharmaceutically acceptable non-toxic acid addition salts and carboxylic acid salts thereof. Said prior art peptides are described in Veber, U.S. patent application Ser. No. 920,529, filed June 29, 1978.

Said prior art peptides differ from somatostatin by virtue of the fact that they lack an N-terminal amino group thus eliminating the group involved in enzymatic cleavage of the molecule by aminopeptidases. Furthermore, the deletion of the adjacent heteroatoms of the disulfide bridge of somatostatin increases the stability of the analogs in vivo by preventing enzymatic degradation by reductive cleavage. Therefore, said prior art peptides are more resistent to cleavage in vivo that somatostatin and thus have a prolonged duration of action.

The present invention provides peptides having somatostatin activity which are retro-enantiomeric peptides of those prior art peptides set forth in U.S. Ser. No. 920,529, filed June 29, 1978. The term retro-enantiomeric is intended to designate a peptide to which the sequence is reversed and the chirality at each residue is inverted relative to a parent peptide. Shemyakin, et al., Angew Chem., Int. Ed. Engl., 8, 492–499 (1969).

SUMMARY OF THE INVENTION

This invention is concerned with novel peptides having a more specific biological activity and longer duration of activity than naturally occurring somatostatin and which are easier to prepare because of the smaller ring size and having the structural formula:

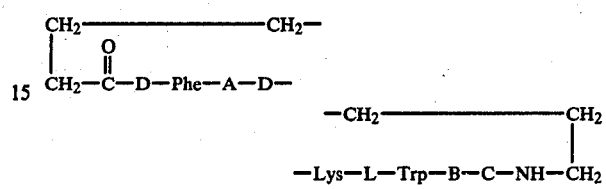

and

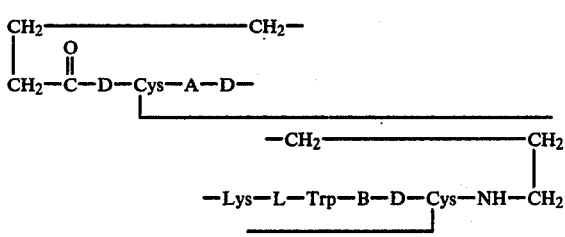

wherein
A is D—Thr, D—Val,
B is D—Phe, D—Tyr,
C is D—Phe, D—Tyr, O—Me—D—Tyr
wherein the ring formed by the peptide backbone contains 26 atoms and pharmaceutically acceptable non-toxic acid addition salts thereof.

The preferred somatostatin analogs of the present invention are illustrated by the following structural formulas:

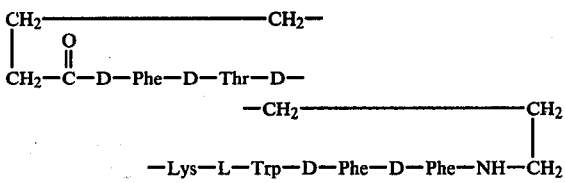

and

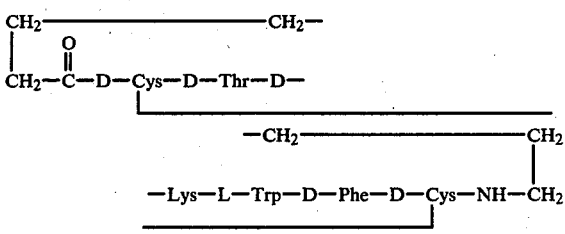

and the pharmaceutically acceptable non-toxic acid addition salts thereof.

Illustrative of acid addition salts are hydrochloride, hydrobromide, sulfate, phosphate, maleate, acetate, citrate, benzoate, succinate, malate, ascorbate and the like. The acid addition salts can be conveniently prepared by dissolving the above novel compounds in water, adding two equivalents of appropriate acid and lyophilizing.

The abbreviated designations, which are used herein for the amino acid components, certain preferred protecting groups, amino acid activating groups, condensing agents, reagents and solvents employed in the process of this invention are as follows:

TABLE I

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| O-Me-Tyr | O-Me-L-tyrosine |
| Val | L-valine |
| D-Lys | D-lysine |
| D-Phe | D-phenylalanine |
| D-Thr | D-threonine |
| D-Tyr | D-tyrosine |
| O-Me-D-Tyr | O-Me-D-tyrosine |
| D-Val | D-valine |
| Cys | L-cysteine |
| D-Cys | D-cysteine |
| Acm-D-Cys | acetamidomethyl-D-cysteine |

| Abbreviated Designation | Protecting Groups |
|---|---|
| BOC | tert-butyloxycarbonyl |
| Bzl | benzyl |
| 2-Cl-CBZ | 2-chlorobenzyloxycarbonyl |
| NHNH$_2$ | hydrazide |

| Abbreviated Designation | Activating Groups |
|---|---|
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |

| Abbreviated Designation | Solvents |
|---|---|
| EPAW | ethyl acetate-pyridine-acetic acid-water |

TABLE I-continued

| BAW | butanol-acetic acid-water |
| CMW | chloroform-methanol-water |
| DMF | dimethylformamide |
| THF | tetrahydrofuran |
| CMA | chloroform-methanol-concentrated NH$_4$OH |

In accordance with the present invention, the novel somatostatin analogs are prepared by cyclizing corresponding linear peptides. The linear peptides are prepared by using the solid phase sequential synthesis technique. Accordingly, the process for preparing the somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic peptide; and (e) removing the remaining blocking groups.

When the linear peptide is prepared on the resin, it is not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. As an example to illustrate this, either of the two following linear peptides, when cyclized, will give the identical somatostatin analog:

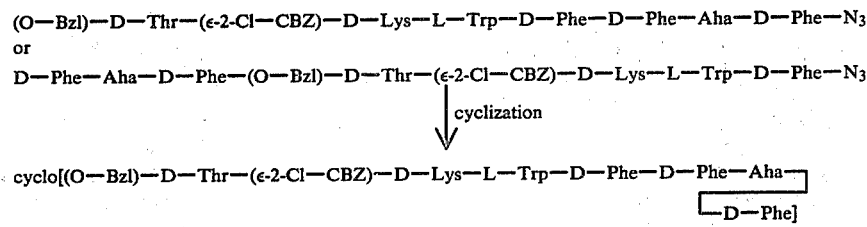

It is evident that since the linear peptide is going to be cyclized, it does not matter which amino acid is used to start the chain. Starting with D-Phe at the carboxyl end, as illustrated in the first of the two examples above, has an advantage over the second example. In the first example, Trp, which reacts with t-butyl carbonium ions formed when BOC groups are removed, is in position closer to the N-terminal amino acid and thus will be subjected to a lesser number of exposures to t-butyl carbonium ion.

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chloride per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e., trifluoro acetic acid, or hydrogen chloride in ethyl acetate).

The —OH group of Thr can be protected by the Bzl group and the ε-amino group of Lys can be protected by the INOC group or the 2-chlorobenzyloxycarbonyl (2—Cl—CBZ) group. In the case of Lys, it is preferred to protect the ε-amino group with 2—Cl—CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, sulfonic, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear hexapeptide. In the case wherein the ester is the methyl ester, the resulting compound may be converted to the azide via the hydrazide which may then be cyclized to the desired cyclic peptide. The preferred method in the present invention is the use of hydrazine.

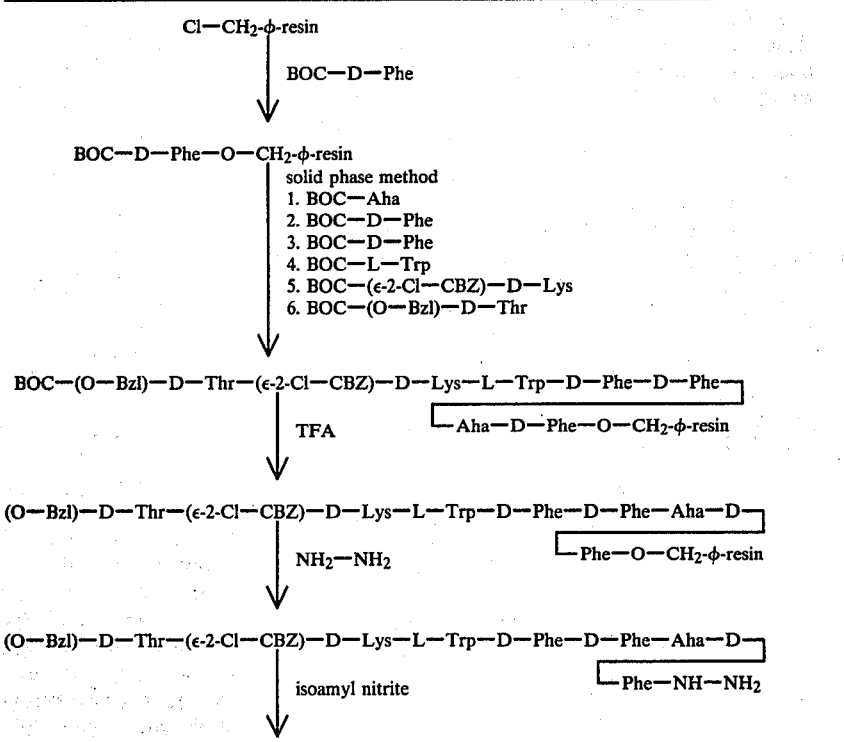

TABLE II

General Scheme for Preparing
cyclo(D—Thr—D—Lys—Trp—D—Phe—D—Phe—Aha—D—Phe)

TABLE II-continued

General Scheme for Preparing
cyclo(D—Thr—D—Lys—Trp—D—Phe—D—Phe—Aha—D—Phe)

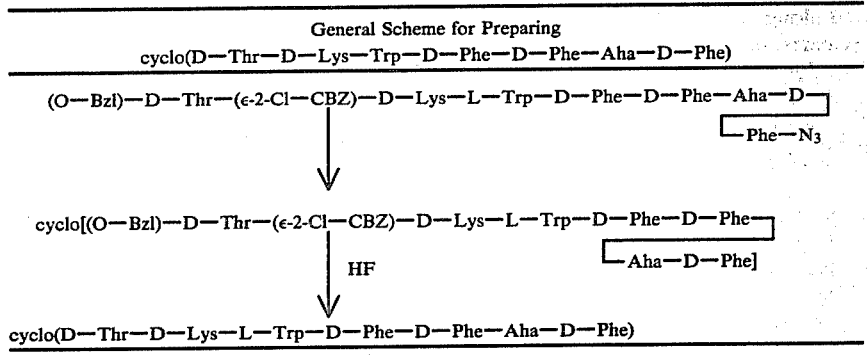

cyclo(D—Thr—D—Lys—L—Trp—D—Phe—D—Phe—Aha—D—Phe)

As reference to Table II will show, one preferred overall procedure for preparing the desired cyclic peptides of the present invention involves the stepwise synthesis of the linear peptide on a solid phase resin. More specifically, in the process for preparing cyclo(-D—Thr—D—Lys—L—Trp—D—Phe—D—Phe—Aha—D—Phe), the carboxyl end of the N-blocked amino acid D-phenylalanine is bound covalently to an insoluble polymeric resin support as the carboxylic acid ester of the resin-bonded benzyl chloride. The amino group of D-Phe is protected by the BOC group. After the attachment of the D-Phe is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence: (O—Bzl)—D—Thr—(ε—2—Cl—CBZ)—D—Lys—L—Trp—D—Phe—D—Phe—Aha—D—Phe—$NHNH_2$ is treated with isoamyl nitrite in acid pH to form the corresponding azide. The azide solution is diluted with solvent and neutralized with an organic base. The linear peptide cyclizes to form cyclo[(O—Bzl)—D—Thr—(ε—2—Cl—CBZ)—D—Lys—L—Trp—D—Phe—D—Phe—Aha—D—Phe]. During the cyclization the "pH" is checked and maintained at neutral by the addition of organic base. The "pH" in organic solvent is determined by the application of an aliquot of the solution to wet narrow range pH paper.

After the linear peptide is cyclized, the remaining protective groups, 2—Cl—CBZ and Bzl, are removed in one step by treatment with HF in the presence of anisole. The crude cyclic peptides obtained by the processes of Table II are purified by chromatography, preferably on Sephadex eluted with 50% aqueous acetic acid.

In case of a monocyclic peptide containing two Acm—D—Cys amino acids, the monocyclic peptide is converted to a bicyclic structure such as

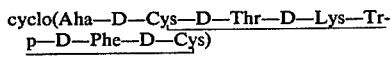

by removal of the Acm blocking groups from D—Cys and formation of a disulfide bridge between the two cysteines by treatment with $I_2$ in DMF. The crude bicyclic peptide is purified by silica gel chromatography and filtration through Sephadex.

The following examples illustrate methods of carrying out the present invention, but it is to be understood that these examples are given for purposes of illustration and not of limitation. It is to be understood that by changing the amino acid sequence of the polypeptide in accordance with the instructions provided by this disclosure, affords each of the compounds embraced by the description presented herein and embraced by the claims of this application.

EXAMPLE 1

Preparation of
cyclo(D—Thr—D—Lys—L—Trp—D—Phe—D—Phe—Aha—D—Phe)

Step (a)—Preparation of (O—Bzl)—D—Thr—(ε—2—Cl—CBZ)—D—Lys—L—Trp—D—Phe—D—Phe—Aha—D—Phe—O—$CH_2$—φ—resin Chloromethyl resin (2% cross-linked Merrifield resin), 100 g (0.264 moles), having 2.64 meq. chlorine/g, and 70 g (0.264 moles, 1 equivalent) of BOC—D—Phe were added to 600 ml of peroxide-free tetrahydrofuran. The mixture was stirred in an oil bath at 80° C. bath temperature for 45 minutes. Triethylamine, 34.8 ml, was added and the reaction mixture stirred at 80° C. bath temperature for 60 hours, cooled to 25° C. and transferred to a solid phase reaction vessel with 500 ml of tetrahydrofuran. After removal of the solvent, the resin was washed using a manual shaker with:

| | |
|---|---|
| 1 1 | MeOH |
| 2 × 1 1 | DMF |
| 2 × 1 1 | MeOH · $H_2O$ (1:1) |
| 2 × 500 ml | HOAc |
| 2 × 500 ml | MeOH |
| 2 × 750 ml | $CH_2Cl_2$ |

The BOC—D—Phe—O—$CH_2$—φ-resin was dried in vacuo at 25° C. for 16 hours, giving 137.11 g of BOC—D—Phe—O—$CH_2$—φ-resin containing 1.14 mmole of D-phenylalanine/g of resin.

BOC—D—Phe—O—$CH_2$—φ-resin (1.75 g, 2.0 mmole) was carried through the procedures in Tables IV and V using 2 deblockings (2 minutes and 25 minutes) with 25% TFA in methylene chloride, and 2.5 equivalents of BOC-amino acid in the required sequence until the desired BOC—heptapeptide—O—$CH_2$—φ-resin was obtained. After the L-Trp has been incorporated, further deblocking steps are carried out in the presence of 1% ethanedithiol.

DCCI was used as the coupling agent in every step except the coupling of BOC—D—Phe to Aha—D—Phe—O—CH₂—φ-resin, in which case the coupling was carried out in the presence of DCCI and 1-hydroxybenzotriazole monohydrate (HBT.H₂O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the ε-amino group of Lys with 2—Cl—CBZ.

When the desired BOC—heptapeptide—O—CH₂—φ-resin was obtained, the N-terminal BOC group was removed by the terminal deblocking procedure set forth in Table VI.

resin was filtered and dried overnight in vacuo. It weighed 3.86 g.

Step (b)—Preparation of (O—Bzl)—D—Thr—(ε—2—Cl—CBZ)—D—Lys—L—Trp—D—Phe—D—Phe—Aha—D—Phe—NHNH₂

A suspension of 3.7 g of (O—Bzl)—D—Thr—(ε—2—Cl—CBZ)—D—Lys—L—Trp—D—Phe—D—Phe—Aha—D—Phe—O—CH₂—φ-resin in 37 ml DMF and 3.7 ml hydrazine was stirred at room temperature for 1 hour and filtered. The insoluble resin was washed with 4 portions of 20 ml of DMF and the combined filtrates concentrated in vacuo to an oil. The crude product was triturated with 2 portions of 35 ml of ether, filtered, dried in vacuo for 30 minutes and washed with 4 portions of 20 ml of H₂O to give 1.95 g of the title hydrazide after drying.

Step (c)—Preparation of cyclo[(O—Bzl)—D—Thr—(ε—2—Cl—CBZ)—D—Lys—L—Trp—D—Phe—D—Phe—Aha—D—Phe]

A solution of 1.85 g of (O—Bzl)—D—Thr—(ε—2—Cl—CBZ)—D—Lys—Trp—D—Phe—D—Phe—Aha—D—Phe—NHNH₂ in 30 ml DMF at −25°

TABLE IV

| Solvent or reagent (number of treatments or washes) | CHCl₃ (2) | 25% TFA in CH₂Cl₂ (2) | CHCL₃ (3) | NEt₃ CH₂Cl₂ (1:9) (2) | CHCl₃ (3) CH₂Cl₂ (3) | BOC AA in CH₂Cl₂, DMF or a mixture of both | 0.5M DCCI in CH₂Cl₂ | DMF (1) MeOH (1) DMF (1) MeOH (1) CHCl₃ (2) |
|---|---|---|---|---|---|---|---|---|
| Volume in ml. | 40 | 40 | 40 | 40 | 40 | 25 ml. | 10 | 40 |
| Time in min. | 5 | 2 and 25 | 2 | 5 and 5 | 2 | 5 | 5 min. coupling 30 min. | 2 |

TABLE V

| Protected Amino Acid | Solvent ml |
|---|---|
| BOC-Aha (1.23 g) recouple | CH₂Cl₂, 25 ml |
| BOC-D-Phe (1.33 g) + HBT · H₂O (1.53 g) recouple | DMF, 25 ml |
| BOC-D-Phe (1.33 g) recouple | CH₂Cl₂, 25 ml |
| BOC-L-Trp (1.52 g) recouple | DMF, 5.5 ml CH₂Cl₂, 19.5 ml |
| BOC-(ε-2-Cl-CBZ)-D-Lys (2.08 g) recouple | CH₂Cl₂, 25 ml |
| BOC-(O-Bzl)-D-Thr (1.55 g) recouple | CH₂Cl₂, 25 ml |

TABLE VI

TERMINAL DEBLOCKING PROGRAM

| Solvent or reagent (number of treatments or washes | CHCl₃ (1) | 25% TFA in CH₂Cl₂ + 1% Ethanedithiol (2) | CHCl₃ (3) | MeOH (2) CH₂Cl₂ (1) MeOH (2) CH₂Cl₂ (2) |
|---|---|---|---|---|
| Vol. in ml. | 60 | 60 | 60 | 60 |
| Time in minutes | 5 | 2 and 25 | 2 | 2 |

After the sequence of Tables IV, V and VI were completed, the blocked heptapeptide—O—CH₂—φ-

C. was acidified with 2.0 ml of 6.19 M HCl in THF and treated with 0.28 ml isoamyl nitrite for 30 minutes. The acidic azide solution was added to 1700 ml of degassed DMF at −40° C. and neutralized with 2.48 ml DIPEA. The solution was kept at −18° C. for 20 hours and at 5° C. for 24 hours during which period an additional 0.9 ml DIPEA was added to keep pH at 7.2–7.6, as measured by moist pH paper, range 6–8. The cyclic product was isolated by evaporation of solvent and trituration of the residual oil with ice water to give 1.82 g of the title product after drying.

Step (d)—Preparation of cyclo(D—Thr—D—Lys—L—Trp—D—Phe—D—Phe—Aha—D—Phe)

A suspension of 1.75 g of cyclo[(O—Bzl)—D—Thr—(ε—2—Cl—CBZ)—D—Lys—L—Trp—D—Phe—D—Phe—Aha—D—Phe] in 3 ml anisole was treated with 30 ml HF at 0° C. for 1 hour. The product was isolated by the removal of HF in vacuo and trituration of the residual gum with EtOAc to give 1.08 g of crude product. Purification by filtration through a Sephadex G-50F (50% HOAc) 5×100 cm column collecting 16.5 ml fractions/10 minutes and combining fractions 101-110 resulted in 520 mg of product, R_f 0.46, 80:20:2, (CMA)
R_f 0.84, 10:5:1:3, (EPAW)
[α]_D +37.1 (c 0.25, 50% AcOH).

A 20 hour acid hydrolysate showed the following amino acid analysis:

|  | Normalized to Average |
|---|---|
| Lys | 0.98 |
| Thr | 1.01 |
| Phe | 3.01 |
| Trp | 1.06 (U.V.) |
| Aha | 1.19 |

EXAMPLE 2

Preparation of cyclo(Aha—D—Cys—D—Thr—D—Lys—Trp—D—Phe—D—Cys

The desired compound is prepared by essentially the same experimental procedure as described for Example 1. The hexapeptide-resin is prepared by the described solid phase method starting with BOC—D—Phe-resin and coupling sequentially with BOC—Trp, BOC—(-ε—2—Cl—CBZ)—D—Lys, BOC—(O—Bzl)—D—Thr, BOC—(Acm)—D—Cys, BOC—Aha, and BOC—(Acm)—D—Cys. After removal of the linear peptide from the resin by hydrazinolysis, azide cyclization, and removal of the D—Lys and D—Thr blocking groups by HF, the two (Acm)—D—Cys residues are converted to D-cystine by treatment of the peptide with 6 equivalents of $I_2$ in DMF. Removal of the excess $I_2$ by silica gel chromatography and elution of the column with the solvent 60:40:10, (CMW) provides the desired title compound.

The peptides of the present invention and the non-toxic pharmaceutically acceptable salts thereof, are useful in humans and animals for inhibiting growth hormone release as in the treatment of acromegaly, inhibiting the release of glucagon and alone or in conjunction with insulin, for lowering blood glucose as in the treatment of diabetes with reduced gastrointestinal side effects. In the treatment of diabetes, the number and size of daily doses and the time of administration are determined by an individual study of each subject. The method of determining these factors is known to those skilled in the art.

The peptides described herein may be administered to warm blooded animals, including humans, either intravenously, subcutaneously, intramuscularly or orally. The contemplated dose range for oral administration in tablet or capsule form to large mammals is about 0.001 mg to about 7 mg/kg of body weight per day. These peptides are preferably administered by injection. A therapeutically effective amount of the peptide is ordinarily supplied at a dosage level of from about 0.001 mg to about 2 mg/kg of body weight. Preferably the range is from about 0.00142 mg to about 0.428 mg/kg of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch, and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of cyclo(D—Thr—D—Lys—L—Trp—D—Phe—D—Phe—Aha—D—Phe) suitable for subcutaneous injection.

EXAMPLE 3

| 1 ml | sterile saline; |
|---|---|
| 1 mg | cyclo(D-Thr-D-Lys-L-Trp-D-Phe-D-Phe-Aha-D-Phe). |

What is claimed is:

1. Compounds of the formula:

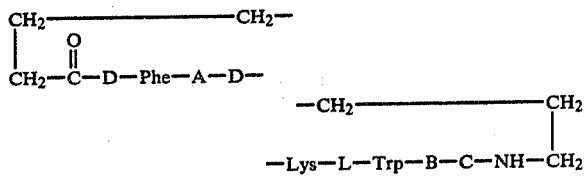

and

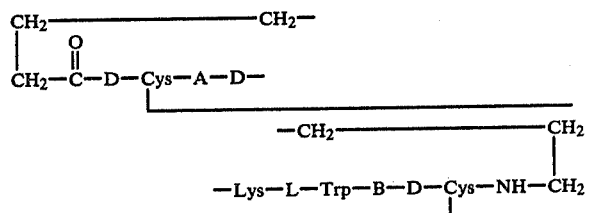

wherein
A is D—Thr, D—Val;
B is D—Phe, D—Tyr;
C is D—Phe, D—Tyr, O—Me—D—Tyr;
wherein the ring formed by the peptide backbone contains 26 atoms and pharmaceutically acceptable non-toxic acid addition salts thereof.

2. The compounds according to claim 1 having the formula:

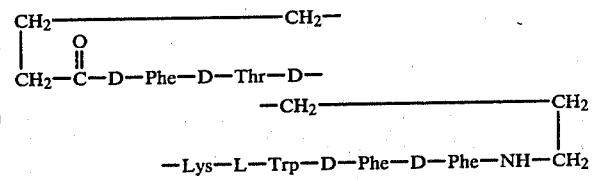

and

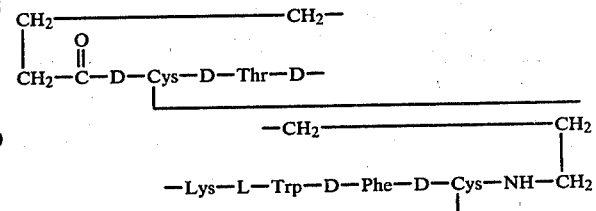

and the pharmaceutically acceptable non-toxic acid addition salts thereof.

3. A composition comprising a therapeutically effective amount of the peptides having the structure:

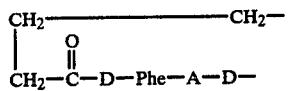
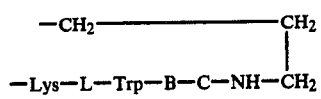
and
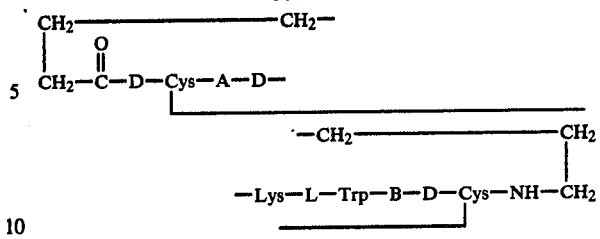
wherein
 A is D—Thr, D—Val,
 B is D—Phe, D—Tyr,
 C is D—Phe, D—Tyr, O—Me—D—Tyr
wherein the ring formed by the peptide backbone contains 26 atoms and pharmaceutically acceptable non-toxic acid addition salts thereof in a pharmaceutically acceptable excipient.
* * * * *